(12) United States Patent
Chen

(10) Patent No.: US 8,827,898 B2
(45) Date of Patent: Sep. 9, 2014

(54) ASSEMBLY FOR ENDOSCOPE

(75) Inventor: Sung-Nan Chen, Taoyuan County (TW)

(73) Assignee: Medical Intubation Technology Corporation, Taoyuan County (TW)

( * ) Notice: Subject to any disclaimer, the term of this patent is extended or adjusted under 35 U.S.C. 154(b) by 473 days.

(21) Appl. No.: 13/019,710

(22) Filed: Feb. 2, 2011

(65) Prior Publication Data
US 2012/0136210 A1 May 31, 2012

(30) Foreign Application Priority Data
Nov. 30, 2010 (TW) .............................. 99141575 A

(51) Int. Cl.
*A61B 1/06* (2006.01)
*G02B 23/24* (2006.01)
*A61B 1/00* (2006.01)
*A61B 1/04* (2006.01)

(52) U.S. Cl.
CPC ........ *G02B 23/2476* (2013.01); *A61B 1/00137* (2013.01); *A61B 1/00177* (2013.01); *A61B 1/00105* (2013.01)
USPC .......................................... 600/175; 600/129

(58) Field of Classification Search
CPC ............. A61B 1/00073; A61B 1/0008; A61B 1/00101; A61B 1/00188
USPC ......... 600/170, 175, 127, 129, 163, 167, 172, 600/174; 411/191, 222, 223, 235; 359/822, 359/823, 825, 827, 829
See application file for complete search history.

(56) References Cited

U.S. PATENT DOCUMENTS

| 5,002,042 | A | * | 3/1991 | Okada ........................... 600/127 |
| 5,215,077 | A | * | 6/1993 | Oku ............................... 600/175 |
| 5,299,067 | A | * | 3/1994 | Kutz et al. ..................... 359/827 |
| 5,644,438 | A | * | 7/1997 | Pottash .......................... 359/798 |

\* cited by examiner

*Primary Examiner* — Alireza Nia
(74) *Attorney, Agent, or Firm* — Muncy, Geissler, Olds & Lowe, P.C.

(57) ABSTRACT

An assembly for the endoscope is composed of a tubular member, a positioning ring, and a sleeve. The tubular member on its external wall includes a first threaded portion and a second threaded portion spaced from the first threaded portion. The positioning ring includes a threaded part formed on an internal wall thereof for axial movement along the tubular member. The sleeve includes a threaded section formed on an internal wall thereof. When the sleeve is sleeved onto the tubular member, the threaded section is located between the first and second threaded portions and stopped against the first threaded portion; meanwhile, the positioning ring can be pushed against the sleeve to fasten the sleeve onto the tubular member. Accordingly, the sleeve can be accurately, rapidly, and conveniently positioned onto the tubular member.

9 Claims, 4 Drawing Sheets

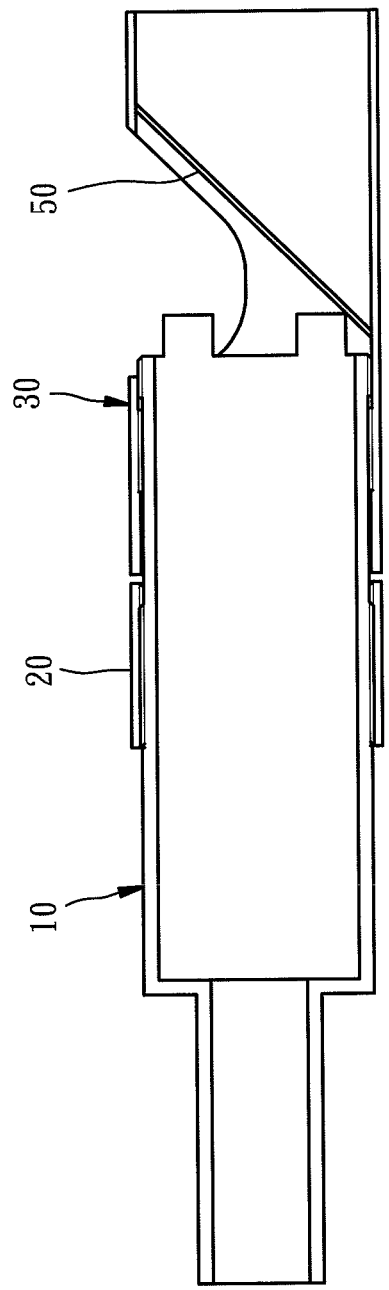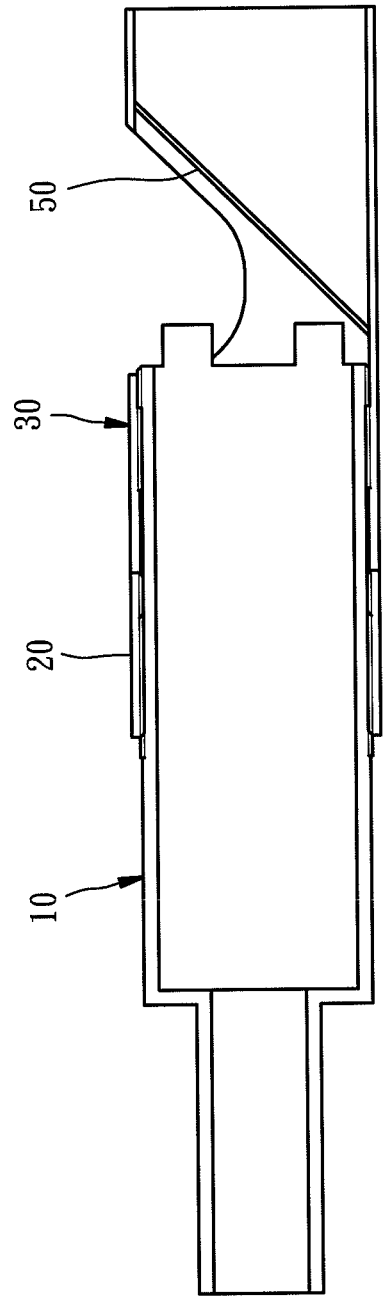
FIG. 3A
FIG. 3B

ASSEMBLY FOR ENDOSCOPE

BACKGROUND OF THE INVENTION

1. Field of the Invention

The present invention relates generally to a medical apparatus, and more particularly, to an assembly for an endoscope.

2. Description of the Related Art

Referring to FIG. 4, a conventional assembly 40 for an endoscope is composed of a hollow tube 41, a positioning ring 43, and a sleeve-shaped side-view member 45 mounted to the hollow tube 41 in such a way that lateral photography can be done. The hollow tube 41 includes a continuous thread 411 formed on an external wall thereof, an optical camera lens (not shown) and a lighting member (not shown), which are mounted to a first opening 413 thereof, and a cable (not shown) extending out of a second opening 15 thereof. The positioning ring 43 includes a thread formed on an internal wall thereof. The side-view member 45 includes a thread formed on an internal wall thereof, a light hole 451 running through a sidewall thereof, and a fully reflecting mirror (not shown) slantingly mounted therein and corresponding to the light hole 451 for reflecting lateral images to the optical camera lens.

Because the positioning ring 43 and the side-view member 45 are sleeved onto the hollow tube 41 and moved to be reversely threaded with the thread 411 separately to position the side-view member 45 onto the hollow tube 41, it is a little inconvenient for assembly and positioning. Besides, where the aforesaid two components are stopped against each other fails to be accurately fastened to result in that the viewable area of the camera lens is too small when the side-view member 45 is too close to the first opening 413 and that the side-view member 45 is subject to disengagement from the hollow tube 41 due to insecure threaded connection when the side-view member 45 is too far from the first opening 413. Even if the hollow tube 41 is marked to fasten the distance between the side-view member 45 and the first opening 413, it is still necessary to move the positioning ring 43 and the side-view member 45 for positioning, so the operation is still inconvenient.

SUMMARY OF THE INVENTION

The primary objective of the present invention is to provide an assembly for an endoscope, which can do accurate, rapid, and convenient positioning.

The foregoing objective of the present invention is attained by the assembly for the endoscope. The assembly is composed of a tubular member, a positioning ring threadedly sleeved onto the tubular member, and a sleeve threadedly sleeved onto the tubular member. The tubular member on its external wall includes a first threaded portion, a second threaded portion, and a threadless middle portion abutting against and located between the first and second threaded portions. The positioning ring includes a threaded part formed on an internal wall thereof and threadedly connected with the second threaded portion of the tubular member to be moved along the tubular member axially. The sleeve includes an opening and a threaded section formed on an internal wall thereof; the threaded section is shorter than the middle portion and can be threadedly connected with the first threaded portion. In process of assembly, the threaded section can pass through the first threaded portion to be located at the middle portion and stopped against an opposite end of the first threaded portion with respect to the middle portion. And then, the positioning ring can be pushed against the sleeve to fasten the sleeve onto the tubular member. In this way, the sleeve can be accurately positioned onto the tubular member every time. Besides, whenever it is intended for the positioning, it only needs to push the positioning ring against the sleeve, so the positioning can be completed conveniently and rapidly.

Further, the threaded section and the opening of the sleeve are spaced from each other in such a way that the sleeve can be rapidly threadedly sleeved onto the tubular member.

Further, the tubular member includes an opening and a body. The first threaded portion extends from the opening toward the body. The second threaded portion is located at the body.

Further, the second threaded portion has a stopping portion formed at an opposite end thereof with respect to the opening to stop the positioning ring from moving toward a rear end of the tubular member behind the second threaded portion and from disengaging from the tubular member.

Further, the middle portion is smaller than the first and second threaded portions in external diameter; namely, in the sectional view, a surface of the middle portion is lower than surfaces of the first and second threaded portions. Thus, the positioning ring can be slidably moved along the middle portion.

BRIEF DESCRIPTION OF THE DRAWINGS

FIG. 3A is a sectional view of the preferred embodiment of the present invention, illustrating that the threaded section of the sleeve is located at the middle portion of the tubular member.

FIG. 3B is similar to FIG. 3A, illustrating that the positioning ring is pushed against the sleeve.

DETAILED DESCRIPTION OF PREFERRED EMBODIMENTS

Figure 1:
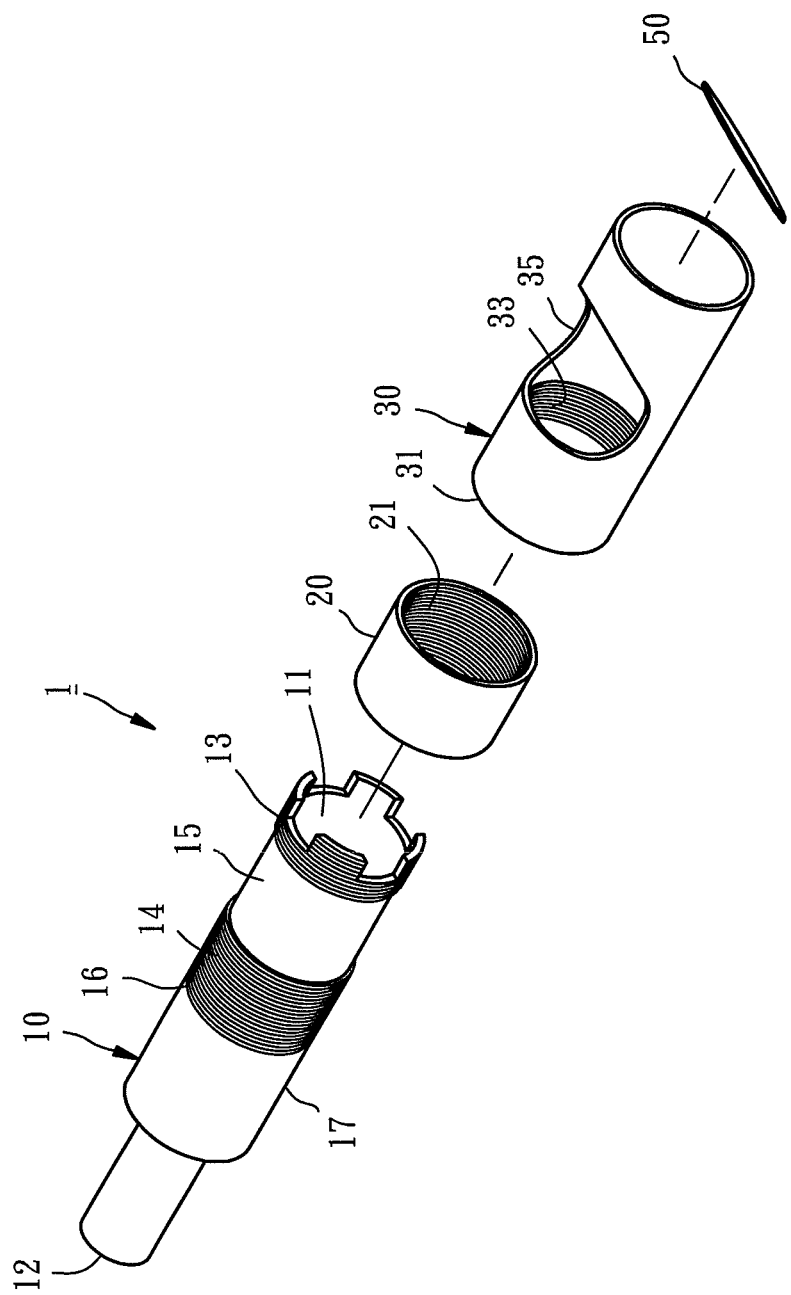
FIG. 1 is an exploded view of a preferred embodiment of the present invention.
Figure 2:
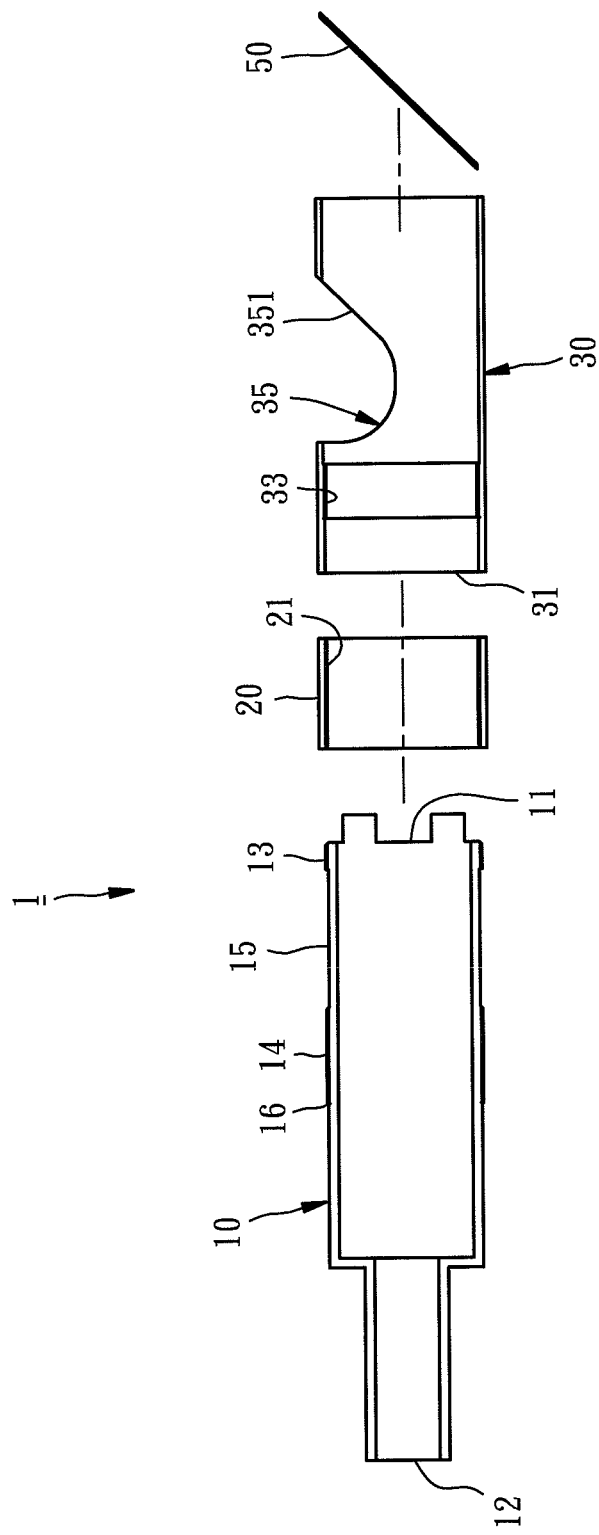
FIG. 2 is a sectional exploded view of the preferred embodiment of the present invention.
Figure 4:
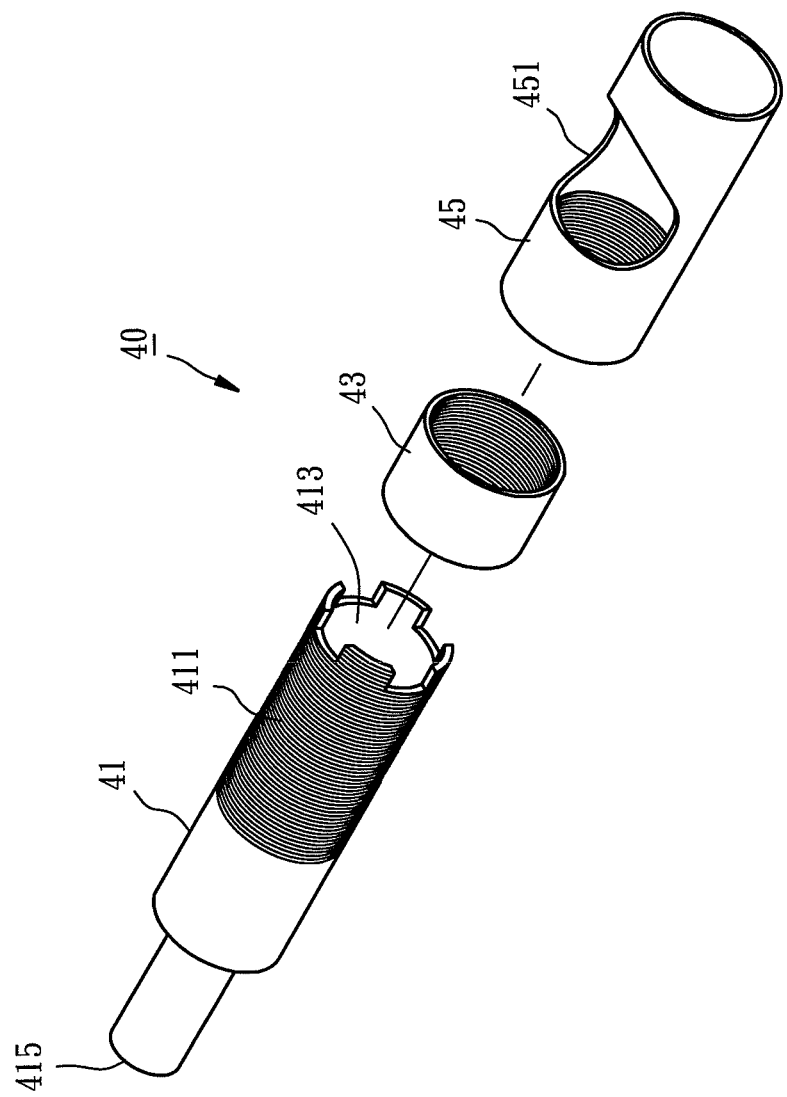
FIG. 4 is an exploded view of the prior art.

Referring to FIGS. 1-2, an assembly 1 for an endoscope in accordance with a preferred embodiment of the present invention is composed of a tubular member 10, a positioning ring 20, and a sleeve 30. The detailed descriptions and operations of these elements as well as their interrelations are recited in the respective paragraphs as follows.

The tubular member 10 is made of metal in one piece and includes a first opening 11, a second opening 12, and a body 17 located between the first and second openings 11 and 12. The tubular member 10 further includes a first threaded portion 13 extending for a predetermined length toward the second opening 12 from the first opening 11, a second threaded portion 14 formed between the first and second openings 11 and 12 and located at the body 17, and a threadless middle portion 15 abutting against and located between the first and second threaded portions 13 and 14. A stopping portion 16 is formed between the second thread 14 and the second opening 12. The external diameter of the middle portion 15 is smaller than those of the first and second threaded portions 13 and 14; namely, the surface of the middle portion 15 in sectional view is lower than those of the first and second threaded portions 13 and 14. In actual application, an optical camera lens (not shown) and an illuminant (not shown) are mounted to the first opening 11 of the tubular member 10 and a cable (not shown) extends out of the second opening 12.

The positioning ring 20 is made of metal in one piece and includes a continuous threaded part 21 formed at an internal wall thereof. In assembly, the threaded part 21 of the positioning ring 20 is threaded with the first threaded portion 13; after the threaded part 21 disengages from the first threaded portion 13, the positioning ring 20 is slidably moved along the middle portion 14; next, as shown in FIG. 3A, the threaded part 21 is threaded with the second threaded portion 14 and stopped by the stopping portion 16 to prevent the positioning ring 20 from disengagement from the tubular member 10 through the second opening 11 and to confine the positioning ring 20 to the second threaded portion 14, and the positioning ring 20 is movable toward the first threaded portion 13. In a word, the positioning ring 20 is axially movable along the tubular member 10 by means of the threaded connection of the tubular member 10 therewith.

The sleeve 30 is made of metal in one piece and includes an opening 31 and a threaded section 33 spaced from the opening 31 in such a way that the sleeve 30 can be rapidly threadedly sleeved onto the tubular member 10. Besides, the threaded section 33 is shorter than that of the middle portion 15 of the tubular member 10 to allow the threaded section 33 to be located at the middle portion 15 while the sleeve 30 is sleeved onto the tubular member 10. It is to be noted that the sleeve 30 is a side-view member in this embodiment, so the sleeve 30 includes a through hole 35 running through an external wall thereof. As shown in FIG. 2, the through hole 35 in sectional view is provided with a bevel 351. In this way, a fully reflecting mirror 50 can be slopingly mounted in the sleeve 30 and correspond to the through hole 35. The front surface of the fully reflecting mirror 50 is parallel to the bevel 31 and faces the opening 31. In actual operation, the sleeve 30 is not limited to the side-view member but any other alternative which can be sleeved onto the tubular member 10.

In addition, it is to be noted that the length of the threaded section 33 can be preferably defined as the distance between the fully reflecting mirror 50 and the optical camera lens located at the first opening 11 when the sleeve 30 is positioned to the tubular member 10; briefly, the viewable area of the optical camera lens is the broadest.

Referring to FIG. 3A again, when the actual assembly is applied, the positioning ring 20 is threadedly sleeved onto the tubular member 10 as per the aforesaid manner and then the threaded section 33 is threaded with the first threaded portion 13. When the sleeve 30 continues to threadedly move toward the positioning ring 20, the threaded section 33 can gradually pass through and disengage from the first threaded portion 13 to be located at the middle portion 15, and meanwhile, the sleeve 30 is rotatable on the tubular member 10 without any movement. Next, as shown in FIG. 3B, make the threaded section 33 be stopped against an opposite end of the first threaded portion 13 with respect to the middle portion 15 and then make the positioning ring 20 threadedly move toward the sleeve 30 to force the positioning ring 20 to push against the sleeve 30 in such a way that the sleeve 30 can be fixed to the tubular member 10.

In conclusion, positioning of the sleeve 30 only needs to let the threaded section 33 of the sleeve 30 be stopped against the first threaded portion 13 of the tubular member 10 to force the positioning ring 20 to push against the sleeve 30, such that the operation is convenient. Besides, whenever the sleeve 30 is mounted to the tubular member 10, the sleeve 30 can be accurately and rapidly fixed to the same position of the tubular member 10.

Although the present invention has been described with respect to a specific preferred embodiment thereof, it is in no way limited to the specifics of the illustrated structures but changes and modifications may be made within the scope of the appended claims.

What is claimed is:

1. An assembly for endoscope, comprising:
    a tubular member at its external wall thereof having a first threaded portion, a second threaded portion, and a threadless middle portion located between the first and second threaded portions;
    a positioning ring having a threaded part formed at an internal wall thereof and threaded with the second threaded portion of the tubular member, the positioning ring being axially movable along the tubular member by means of the aforesaid threaded connection; and
    a sleeve having an opening and a threaded section formed at an internal wall thereof, the threaded section being shorter than the middle portion, the sleeve being threadedly sleeved onto the tubular member through the opening, the threaded section being located at the middle portion of the tubular member, the threaded section being stopped against an opposite end of the first threaded portion with respect to the middle portion, the positioning ring having a distal end pushed distally against the sleeve to position the sleeve onto the tubular member.

2. The assembly as defined in claim 1, wherein the tubular member comprises an opening and a body; the first threaded portion extends toward the body from the opening; the second threaded portion being located at the body.

3. The assembly as defined in claim 2, wherein the tubular member comprises a stopping portion located at an opposite end of the second threaded portion with respect to the opening for stopping the positioning ring from disengagement from the tubular member toward its rear end behind the second threaded portion.

4. The assembly as defined in claim 1, wherein the middle portion is smaller than the first and second threaded portions in external diameter to allow the positioning ring to be slidably moved along the middle portion.

5. The assembly as defined in claim 1, wherein threaded section of the sleeve is spaced from the opening.

6. The assembly as defined in claim 5, wherein the sleeve comprises a through hole running through an external wall thereof, a fully reflecting mirror being mounted in the sleeve and corresponding to the through hole.

7. The assembly as defined in claim 6, wherein the sleeve comprises a bevel formed at the through hole in sectional view; the fully reflecting mirror comprises a front surface aligned with the bevel.

8. The assembly as defined in claim 1, wherein external diameters of the first threaded portion and the second threaded portion are equal.

9. The assembly as defined in claim 1, wherein the sleeve is threadedly sleeved directly onto the tubular member through the opening.

* * * * *